United States Patent [19]

Yamagishi

[11] Patent Number: 5,337,018
[45] Date of Patent: Aug. 9, 1994

[54] ELECTRONIC SENSOR FOR DETERMINING ALCOHOL CONTENT OF FUELS

[75] Inventor: Frederick G. Yamagishi, Newbury Park, Calif.

[73] Assignee: Hughes Aircraft Company, Los Angeles, Calif.

[21] Appl. No.: 976,074

[22] Filed: Nov. 13, 1992

[51] Int. Cl.$^5$ .................. G01N 27/12; G01R 27/22
[52] U.S. Cl. .................. 324/693; 324/446; 324/722; 204/412; 73/61.43
[58] Field of Search ............ 324/439, 441, 446, 693, 324/698, 722, 724, 71.1; 73/61.43; 204/408, 412

[56] References Cited

U.S. PATENT DOCUMENTS

| | | |
|---|---|---|
| 3,567,383 | 3/1971 | Langley et al. ............ 324/693 X |
| 3,710,237 | 1/1973 | Watson et al. ............ 324/446 |
| 4,791,374 | 12/1988 | Yodice et al. ............ 324/439 |
| 5,023,133 | 6/1991 | Yodice et al. ............ 428/332 |
| 5,071,770 | 12/1991 | Kolesar, Jr. ............ 324/439 X |
| 5,089,780 | 2/1992 | Megerle ............ 324/448 |
| 5,109,202 | 4/1992 | Akiba ............ 324/693 |
| 5,196,801 | 3/1993 | Nogami et al. ............ 324/663 |

FOREIGN PATENT DOCUMENTS

0442314A2 8/1991 European Pat. Off. ..... G01N 27/12
0499841 8/1992 European Pat. Off. .

OTHER PUBLICATIONS

Database WPI Week 9225, Derwent Publications Ltd., London, GB; AN 92-203418 & JP-A-4 131 755 (Nippon Telegraph & Telephone Corp.), May 6, 1992, abstract.

J. Phys. Chem. 1985, 89, 1441-1447, "Resistance of Polyaniline Films as a Function of Electrochemical Potential and the Fabrication of Polyaniline-Based Microelectronic Devices", E. Paul, et al. (no month).

Synthetic Metals, 13, 1986, 193-205, 'Polyaniline': Protonic Acid Doping of the Emeraldine Form to the Metallic Regime, J. Chiang et al. (no month).

P. N. Bartlett et al, "Conducting Polymer Gas Sensors", in *Sensors and Actuators*, vol. 20, pp. 287-292 (1989) (no month).

*Primary Examiner*—Kenneth A. Wieder
*Assistant Examiner*—Glenn W. Brown
*Attorney, Agent, or Firm*—V. D. Duraiswamy; W. K. Denson-Low

[57] ABSTRACT

A sensor (10) is provided, which is based on a conductive polymer (16) as the active material to measure the concentration of alcohol in gasoline. This information is then sent to the engine to immediately adjust the air:fuel ratio, which is critical in these alternate fuel systems for the smooth operation of the engine. The sensor of the invention comprises the conductive polymer and a pair of sensing electrodes (12, 14) associated with the conductive polymer. Most conveniently, the sensing electrodes are arranged in an interdigitated fashion and are coated with the conducting polymer. Certain conducting polymers have been found whose resistance changes as a function of alcohol, e.g., methanol, concentration. Since the resistance of the conducting polymer is related to the alcohol concentration, this information can be processed by a microprocessor, which can then make the necessary adjustments in the air:fuel ratio. The device of this invention can be much smaller and much less expensive than the prior art dielectric-based sensor and yet retain precision and accuracy (±0.5% required) with fast response time.

25 Claims, 1 Drawing Sheet

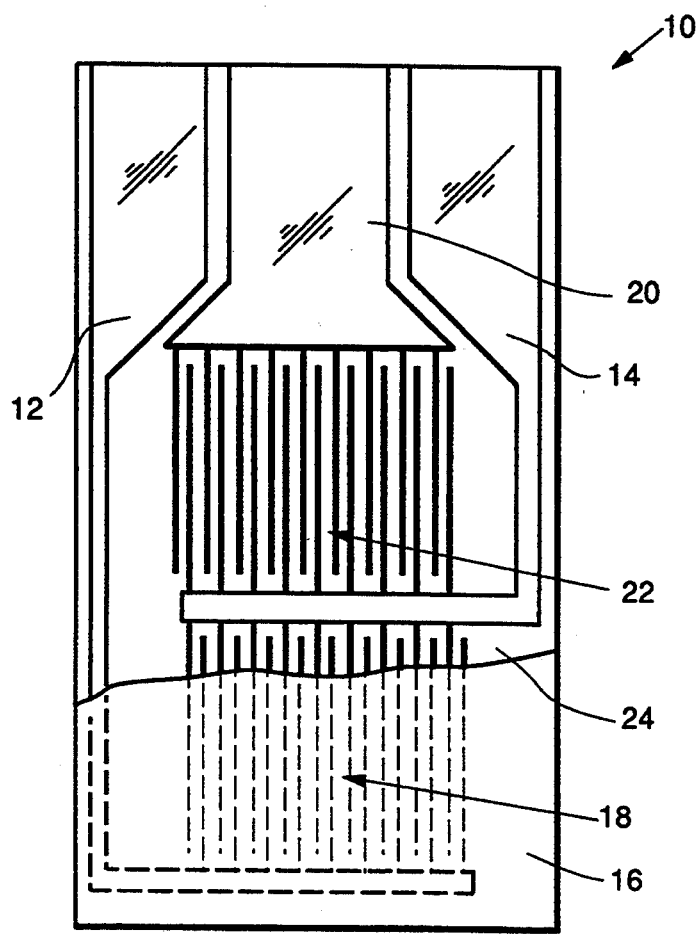
FIG 1.
FIG. 2.
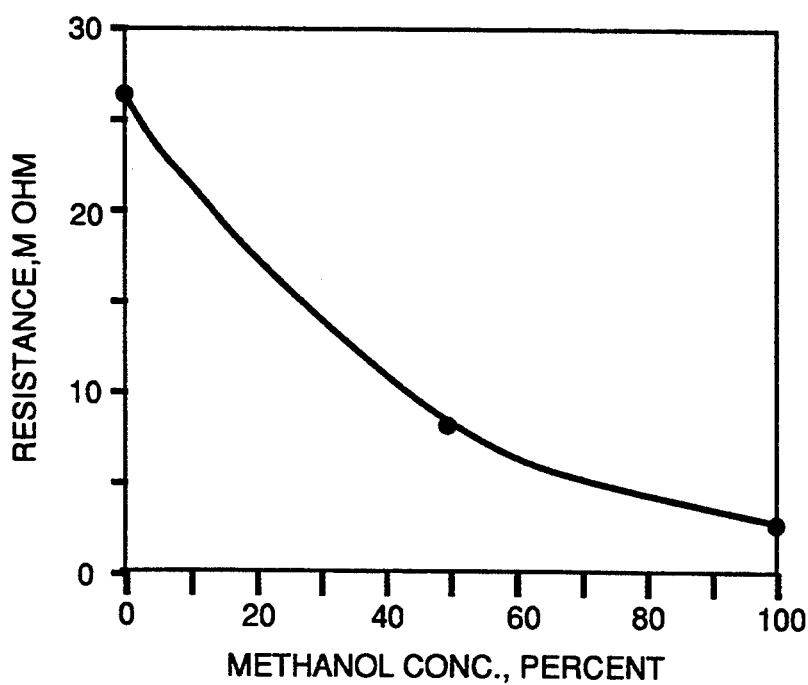

ELECTRONIC SENSOR FOR DETERMINING ALCOHOL CONTENT OF FUELS

BACKGROUND OF THE INVENTION

1. Field of the Invention

The present invention is related to the alcohol-based fuels for automobiles, and, more particularly, to a sensor for determining the alcohol content of such fuels.

2. Description of Related Art

In view of concerns about emissions from automobiles, various alternatives have been proposed. Among the various alternatives is the use of an alcohol-based fuel. While some proposals have set forth methanol or ethanol alone as the fuel, other proposals have suggested a mixture of methanol or ethanol with conventional gasolines.

At the time of this writing, there has been no decision by regulatory groups as to what type of alternate fuels will be required in the future operation of current "gasoline" burning automobiles. California, however, will require that new cars sold in 1994 must have the capability to run on some type of alternate fuel. Should the decision be made that this alternate fuel will be methanol (or ethanol) in gasoline, then a sensor to measure alcohol content in real time will be required for all cars sold in that state. A sensor of this type is of particular importance, since the smooth operation of the engine depends on the proper air:fuel ratio, which is affected strongly by the alcohol content of the fuel. Further, the concentration of alcohol can be expected to vary from one region to another and from evaporation of the alcohol component in the fuel. Since these regulations could result in the installation of millions of units, reducing the size, weight, and cost of these sensors is a major concern of automobile manufacturers.

A prior art sensor currently being used to measure alcohol content is considered to be a state-of-the-art device. The sensor uses the alternate fuel as the dielectric medium of a flow-through capacitor and measures the change in the dielectric constant as a function of alcohol content. This device is relatively large and expensive to manufacture.

Sensors using conductive polymers are well-documented in the literature, including sensors to detect methanol; see, for example, P. N. Bartlett et al, "Conducting Polymer Gas Sensors", *Sensors and Actuators*, Vol. 20, pp. 287-292 (1989) and references cited therein. However, the sensors appear to involve detection of alcohol in the vapor state. While there are examples of conductive polymer sensors operating in aqueous environments, these sensors sense species other than alcohol.

What is required is an alcohol sensor for detecting alcohol (e.g., methanol or ethanol) in a non-aqueous, liquid environment.

SUMMARY OF THE INVENTION

In accordance with the invention, a new sensor is provided, which is based on a conductive polymer as the active material to measure the concentration of alcohol in gasoline. The device described in this invention provides an electronic method for measuring the alcohol content of fuels. This information is then sent to the engine to immediately adjust the air:fuel ratio, which is critical in these alternate fuel systems for the smooth operation of the engine.

The sensor of the invention comprises a conductive polymer which is exposed to the alternate fuel and at least two sensing electrodes shorted by the conductive polymer. Most conveniently, the sensing electrodes are arranged in an interdigitated fashion and are coated with the conducting polymer. Certain conducting polymers have been found whose resistance changes as a function of alcohol, e.g., methanol, concentration.

Since the resistance of the alternate fuel is related to the alcohol concentration, this information can be processed by a microprocessor, which can then make the necessary adjustments in the air:fuel ratio.

The device of this invention can be much smaller and much less expensive than the prior art dielectric-based sensor and yet retain precision and accuracy ($\pm 0.5\%$ required) with fast response time. It can be configured as a small, screw-in arrangement (similar in appearance, for example, to a spark plug) and can be easily installed directly into the fuel rail, immediately in front of the injection system.

BRIEF DESCRIPTION OF THE DRAWINGS

FIG. 1 is a top plan view of an interdigitated sensor of the invention; and

FIG. 2, on coordinates of resistance and concentration, is a plot of the measured resistance of poly(3-methylthiophene) electrochemically deposited on the interdigitated sensor of FIG. 1 as a function of methanol concentration in hexane.

DESCRIPTION OF THE PREFERRED EMBODIMENTS

Referring now to FIG. 1, the sensor 10 presented in this invention is a simple one, using a small, commercially available, microsensor electrode which is patterned with gold, interdigitated electrodes 12, 14 coated with a thin film 16 of conductive polymer (the polymer coating is broken away in FIG. 1 to show the underlying electrodes). One electrode 12 is called the analyte electrode; the second electrode 14 is called the common electrode.

The electrodes 12, 14 may be arranged in an interdigitated fashion, as shown in FIG. 1, or may be in some other configuration, so long as the conductive polymer coating 16 shorts the two electrodes.

The use of two interdigitated electrodes 12, 14, as shown in FIG. 1, provides an analyte area 18. The alcohol-containing fuel interacts with the conducting polymer to change its conductivity, which is a function of the alcohol concentration, as described in greater detail below.

The electrical modulation in conducting polymers is sensitive to temperature, and it may be desirable to provide a means for compensating for operation of the sensor at higher temperature. One way to achieve this is to provide a third reference electrode 20. This reference electrode 20 is interdigitated with the common electrode 14 to provide a reference area 22. The reference area, which is also covered with the conducting polymer 16, is further covered with a non-pervious material (not shown) so as to prevent interaction of the alcohol-containing fuel with the electrodes 14, 20 in the reference area 22. Examples of suitable impervious materials include silicon dioxide, silicon nitride, poly(methylmethacrylate), and poly(styrene). Both electrode areas 18 and 22 experience the safe temperature, but only the analyte area 18 reacts to the alcohol-containing mixture.

The entire assembly is supported on an insulating substrate 24. Examples of suitable substrates include alumina and silica.

The conductive polymers employed in the practice of the present invention are preferably 3-alkyl-substituted polythiophenes. Other conductive polymers may be useful in this application as well, such as polythiophene, although it has been found that the conductivity of polypyrrole was not affected in the presence of methanol. The conductivity of poly(3-methylthiophene) may be modulated by varying the concentration of methanol in hexane (a hydrocarbon solvent used as a substitute for gasoline, a hydrocarbon solvent as well). The conductivity from 0% methanol to 100% methanol changes by a factor of about 9.5 at room temperature, as shown in FIG. 2.

Besides poly(3-methylthiophene), other alkyl-substituted polythiophenes show similar effects; examples of the alkyl substituents include butyl, hexyl, and octyl. The advantage of the longer chain alkyl groups is that the resulting polymers become more soluble the longer the alkyl chain, which is useful in casting thin films of the polymer. As a result, the number of carbon atoms in the alkyl group may range from 0 to 8.

However, longer chain alkyl groups render the polymer soluble in the fuel. Accordingly, it is preferred that the number of carbon atoms in the alkyl group range from 0 to 4.

These as-deposited films are insulators and must be externally "doped" (usually oxidized) to convert them to the conductive state. However, the adhesion of the cast films has been found to be insufficient for practical application. Furthermore, this advantage in processability can become a disadvantage for long term operation if the conductive polymer is slightly soluble in the measurement medium. Depositing the conductive polymer thin film electrochemically results in uniform thin films with much stronger adhesion. Another advantage of this deposition method is that the resulting polymer film is oxidized in situ so that conductive material is obtained directly, and the extra doping step is eliminated. Electrochemical deposition is particularly preferred for preparing thin films of poly(thiophene) and of the lower alkyl forms of poly(3-alkylthiophene). Such electrochemical deposition is well-known in the art, and may be the only way to prepare the afore-mentioned films.

For determining concentration of the alcohol in the alcohol-containing fuel, the conductivity between the two electrodes 12, 14 is measured by conventional means, and does not form a part of this invention. The resulting signal is then further processed to determine the alcohol concentration and to then adjust the air:fuel ratio, as appropriate.

In the temperature-compensated system, the conductivity between the two analyte electrodes 12, 14 and between the two reference electrodes 14, 20 is determined. This measurement is again accomplished by conventional means, and does not form a part of this invention. The resulting signal, as above, is then further processed to determine the alcohol concentration and to then adjust the air:fuel ratio, as appropriate.

Further processing of the resulting signal in either event is done by an engine control module, which compares the signal to previously-stored data of resistance as a function of alcohol concentration. Such signal processing techniques are well-known and do not form a part of this invention.

The sensor 10 of this invention can be much smaller and much less expensive than the prior art dielectric-based sensor and yet retain precision and accuracy ($\pm 0.5\%$ required) with fast response time. The sensor 10 may be configured as a small, screw-in arrangement (similar in appearance, for example, to a spark plug) and can be easily installed directly into the fuel rail, immediately in front of the injection system.

EXAMPLE

A solution containing 3-methylthiophene (Aldrich Chemical, 0.2 M) and dry tetrabutylammonium hexafluorophosphate (Alfa Products, 0.02 M) in nitrobenzene was added to an electrochemical synthesis cell, which was cooled to $\approx 5°$ C. in an ice bath. Into this solution was submerged an interdigitated microsensor electrode (Allage Assoc., Inc.—ABTECH). The electrodes were connected to a dc power supply. Electrochemical deposition was carried out at a current density of 19.8 mA/cm$^2$ (3.0 Vdc, 8.3 mA) for three minutes. The current was then removed and the sensor rinsed with clean nitrobenzene and hexane, then air dried. Conductivity measurements were taken on the dried sensor by submerging it a liquid containing the appropriate concentration of methanol in hexane and measuring the resistance (Triplett Corp. Model 630-PL Multimeter). The results are depicted in FIG. 2 and show that as the methanol concentration increases the resistance decreases. Such calibration data can be stored in the engine control module.

Thus, there has been disclosed an electronic sensor for measuring the alcohol content of fuels. It will be appreciated by those of ordinary skill in this art that various changes and modifications of an obvious nature may be made, and all such changes and modifications are considered to fall within the scope of the invention as defined by the appended claims.

What is claimed is:

1. An electronic sensor for measuring the alcohol concentration of mixtures comprising liquid hydrocarbons and alcohol, comprising:
   (a) at least two electrically conducting electrodes supported on a substrate; and
   (b) a conducting polymer shorting said at least two electrodes, said conducting polymer having a resistance that changes as a function of said alcohol concentration.

2. The electronic sensor of claim 1 wherein said alcohol is selected from the group consisting of methanol and ethanol.

3. The electronic sensor of claim 1 wherein said conducting polymer is selected from the group consisting of poly(3-alkylthiophenes) and poly(thiophene).

4. The electronic sensor of claim 3 wherein said poly(3-alkylthiophenes) comprises a polymer of 3-alkylthiophene having an alkyl group with from 1 to 8 carbon atoms.

5. The electronic sensor of claim 4 wherein said alkyl group has from 1 to 4 carbon atoms.

6. The electronic sensor of claim 1 comprising a third electrode for temperature compensation, with two of said electrodes forming an analyte area for measuring alcohol concentration, one of said two electrodes comprising a common electrode, and with said third electrode, together with said common electrode, forming a reference area for compensating for temperature.

7. The electronic sensor of claim 6 wherein an impervious material protects said reference area from said mixture.

8. The electronic sensor of claim 7 wherein said impervious material is selected from the group consisting of silicon dioxide, silicon nitride, poly(methylmethacrylate), and poly(styrene).

9. An electronic sensor for measuring the methanol content of mixtures comprising gasoline and methanol, comprising:
   (a) three electrically conducting electrodes supported on a substrate, with two of said electrodes forming an analyte area for measuring alcohol concentration, one of said two electrodes comprising a common electrode, and with a third of said electrodes, together with said common electrode, forming a reference area for compensating for temperature; and
   (b) a conducting polymer shorting said three electrodes, said conducting polymer having a resistance that changes as a function of said alcohol concentration.

10. The electronic sensor of claim 9 wherein said conducting polymer is selected from the group consisting of poly(3-alkylthiophenes), said alkyl group containing from 1 to 4 carbon atoms, and poly(thiophene).

11. The electronic sensor of claim 9 wherein an impervious material protects said reference area from said mixture.

12. The electronic sensor of claim 11 wherein said impervious material is selected from the group consisting of silicon dioxide, silicon nitride, poly(methylmethacrylate), and poly(styrene).

13. A method of measuring alcohol concentration in a mixture comprising liquid hydrocarbons comprising:
   (a) providing an electronic sensor comprising
      (1) at least two electrically conducting electrodes supported on a substrate, and
      (2) a conducting polymer shorting said at least two electrodes, said conducting polymer having a resistance that changes as a function of said alcohol concentration;
   (b) exposing said electronic sensor to said mixture to generate a signal that is a function of said resistance; and
   (c) determining said concentration from said signal by comparing said signal to predetermined data relating resistance of said conducting polymer and concentration of said alcohol.

14. The method of claim 13 wherein said alcohol is selected from the group consisting of methanol and ethanol.

15. The method of claim 13 wherein said conducting polymer is selected from the group consisting of poly(3-alkylthiophenes) and poly(thiophene).

16. The method of claim 15 wherein said poly(3-alkylthiophenes) comprises a polymer of 3-alkylthiophene having an alkyl group with from 1 to 8 carbon atoms.

17. The method of claim 16 wherein said alkyl group has from 1 to 4 carbon atoms.

18. The method of claim 17 wherein said conducting polymer is formed as an electrochemically deposited thin film on said substrate.

19. The method of claim 13 wherein said sensor comprises a third electrode for temperature compensation, with two of said electrodes forming an analyte area from which said signal is generated that is used to determine alcohol concentration, said signal constituting a first signal, one of said two electrodes comprising a common electrode which, together with said third electrode, forms a reference area from which a second signal is generated that is used to correct said first signal for temperature of said mixture, whereby said first signal is adjusted by said second signal, forming a resulting signal that is used to determine alcohol concentration as corrected for temperature of said mixture.

20. The method of claim 19 wherein said reference area is covered by an impervious material which protects said reference area from said mixture.

21. The method of claim 20 wherein said impervious material is selected from the group consisting of silicon dioxide, silicon nitride, poly(methylmethacrylate), and poly(styrene).

22. A method for measuring the methanol content of mixtures comprising gasoline and methanol, comprising:
   (a) providing an electronic sensor comprising
      (1) three electrically conducting electrodes supported on a substrate, with two of said electrodes forming an analyte area for measuring alcohol concentration, one of said two electrodes comprising a common electrode, and with a third of said electrodes, together with said common electrode, forming a reference area for compensating for temperature, said reference area protected by a coating impervious to said mixture,
      (2) a conducting polymer shorting said three electrodes, said conducting polymer having a resistance that changes as a function of said alcohol concentration;
   (b) exposing said electronic sensor to said mixture to generate a first signal based on said resistance from said analyte area and to generate a second signal based on said resistance from said reference area;
   (c) correcting said first signal from said analyte area for temperature of said mixture by subtracting said first signal generated from said analyte area from said second signal generated from said reference area to form a resulting signal; and
   (d) determining said concentration from said resulting signal.

23. The method of claim 22 wherein said conducting polymer is selected from the group consisting of poly(3-alkylthiophenes), said poly(3-alkylthiophenes) comprising a polymer of 3-alkylthiophene having an alkyl group with from 1 to 4 carbon atoms, and poly(thiophene).

24. The method of claim 23 wherein said conducting polymer is formed as an electrochemically deposited thin film on said substrate.

25. The method of claim 22 wherein said impervious coating is selected from the group consisting of silicon dioxide, silicon nitride, poly(methylmethacrylate), and poly(styrene).

* * * * *